(12) United States Patent
Wang

(10) Patent No.: US 7,750,304 B2
(45) Date of Patent: Jul. 6, 2010

(54) CONCURRENT RECONSTRUCTION USING MULTIPLE BED FRAMES OR CONTINUOUS BED MOTION

(75) Inventor: Wenli Wang, Aurora, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 461 days.

(21) Appl. No.: 11/721,718

(22) PCT Filed: Dec. 5, 2005

(86) PCT No.: PCT/IB2005/054067

§ 371 (c)(1),
(2), (4) Date: Jun. 14, 2007

(87) PCT Pub. No.: WO2006/064401

PCT Pub. Date: Jun. 22, 2006

(65) Prior Publication Data

US 2009/0238337 A1   Sep. 24, 2009

Related U.S. Application Data

(60) Provisional application No. 60/636,218, filed on Dec. 15, 2004.

(51) Int. Cl.
*G01N 23/04* (2006.01)
(52) U.S. Cl. ............................... 250/363.04; 250/361 R; 250/362; 250/363.03; 382/131
(58) Field of Classification Search ....... 250/361 R–363.09; 382/131
See application file for complete search history.

(56) References Cited

U.S. PATENT DOCUMENTS

| | | | |
|---|---|---|---|
| 5,331,553 A * | 7/1994 | Muehllehner et al. | 250/363.02 |
| 5,744,802 A | 4/1998 | Muehllehner et al. | |
| 6,332,035 B1 * | 12/2001 | Basu et al. | 382/128 |
| 6,727,502 B1 * | 4/2004 | Matthews et al. | 250/363.03 |
| 7,498,581 B2 * | 3/2009 | Wang et al. | 250/363.04 |
| 2003/0161521 A1 | 8/2003 | Newport et al. | |
| 2003/0190065 A1 | 10/2003 | Hamill et al. | |
| 2004/0174960 A1 * | 9/2004 | Hsieh et al. | 378/210 |
| 2007/0018108 A1 * | 1/2007 | Kitamura | 250/363.02 |

FOREIGN PATENT DOCUMENTS

JP   2004061113 A   2/2004

OTHER PUBLICATIONS

Jeng et al. "Overlapping FORE and OSEM for 3D PET Image Reconstruction." Biomed. Eng. Appl. Basis Comm. 2004 (Oct.) 16: 238-243.*

(Continued)

*Primary Examiner*—David P Porta
*Assistant Examiner*—Casey Bryant

(57) ABSTRACT

In an imaging system (10), a short axial length 4D sinograms are loaded one at a time from a data memory (40). A portion of an image memory (44) that corresponds to a currently reconstructed sinogram subset (1112), is initialized. If a part of the object is already reconstructed, an iterative reconstruction is performed in which the previously reconstructed image (m1) is iteratively improved by using the data from the currently reconstructed overlapping image (m2) to converge on the final image.

23 Claims, 9 Drawing Sheets

OTHER PUBLICATIONS

Figure 1:
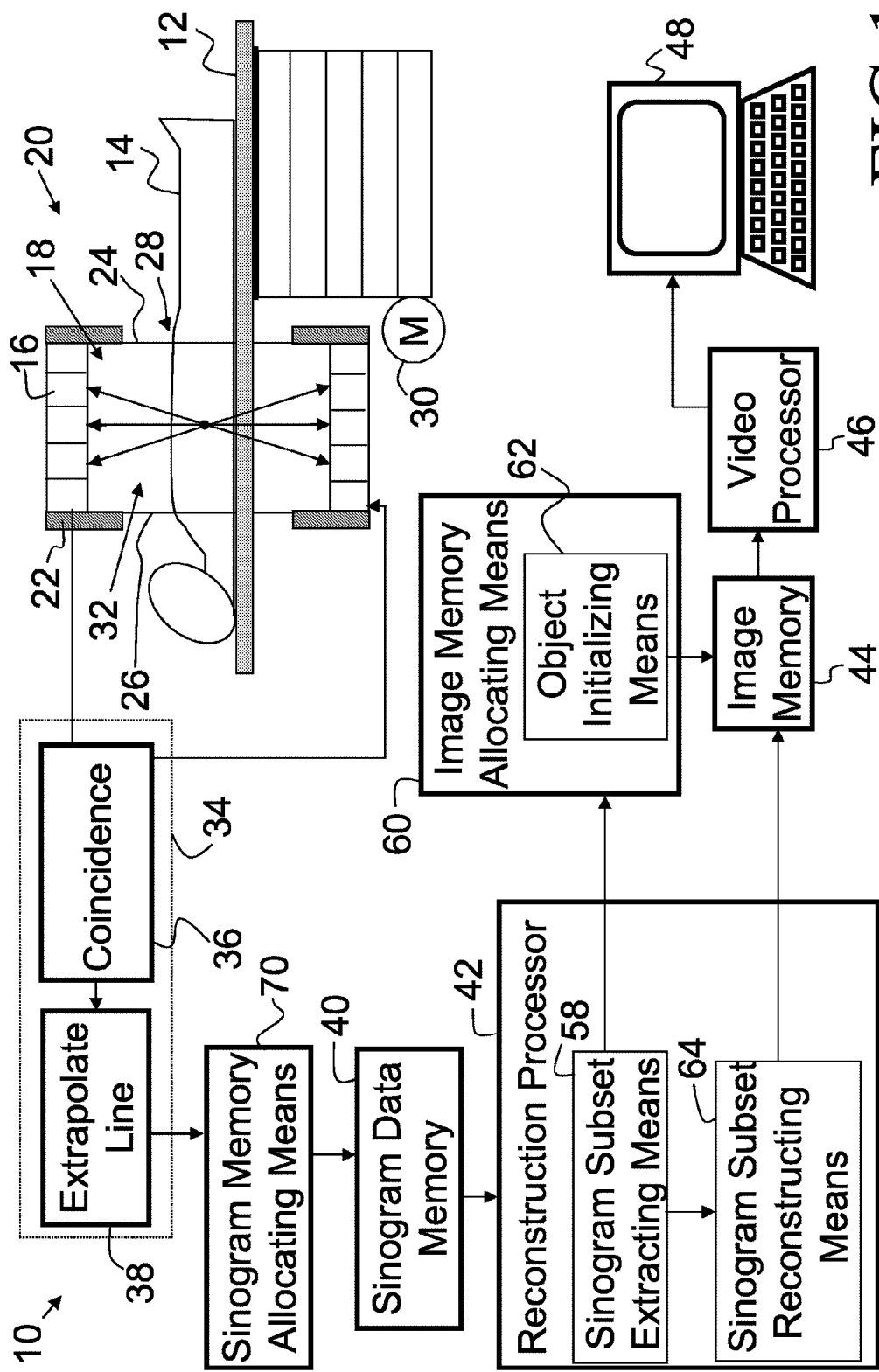

Fahey, F. H.; Data acquisition in PET imaging; 2002; J. of Nuclear Medicine Technology Soc. Nucl. Med.; 30(2)39-49.

Hudson, H. M., et al.; Accelerated image reconstruction using ordered subsets of projection data; 1994; IEEE Trans. on Medical Imaging; 13(4)601-609.

Kinahan, P. E., et al.; Fast iterative image reconstruction of 3D PET data; 1996; IEEE Conf. Record Nuclear Science Symposium; vol. 3; pp. 1918-1922.

Kitamura, K., et al.; Implementation of continuous 3D whole-body PET scanning using on-the-fly Fourier rebinning; 2002; Physics in Medicine and Biology; 47(15)2705-2712.

Wu, T., et al.; Digital tomosynthesis mammography using a parallel maximum likelihood reconstruction method; 2004; SPIE-Int'l. Soc for Optical Engineering; 5368(1)1-11.

\* cited by examiner

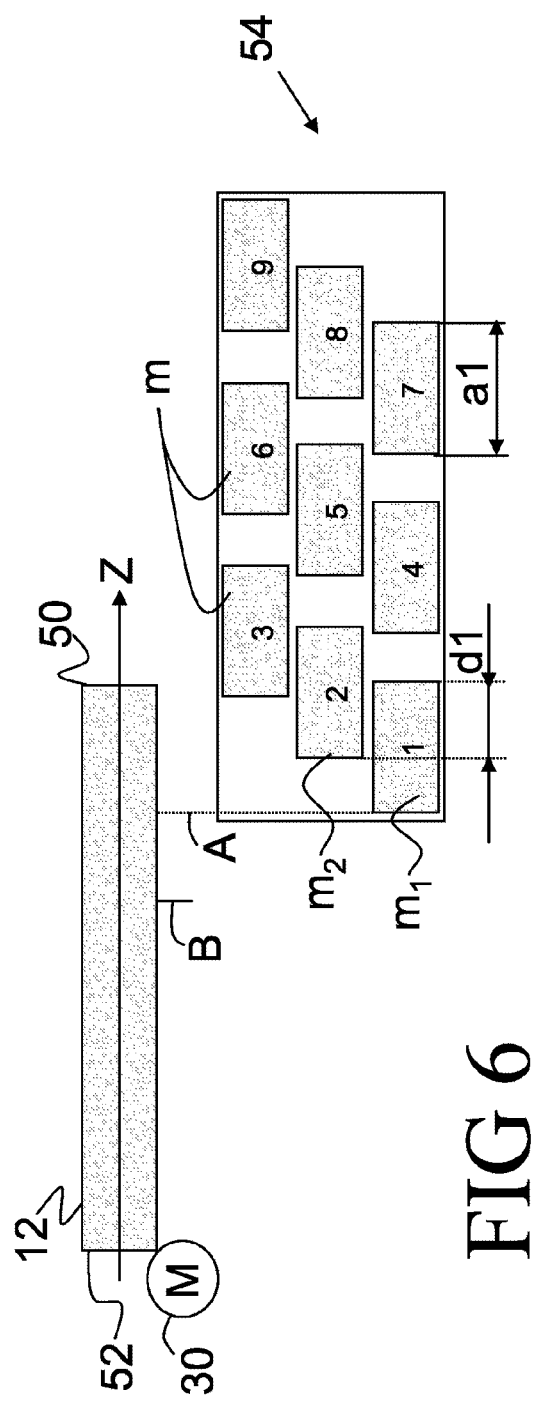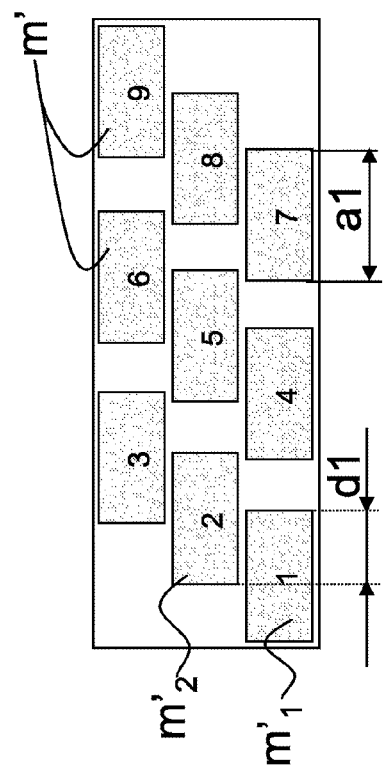

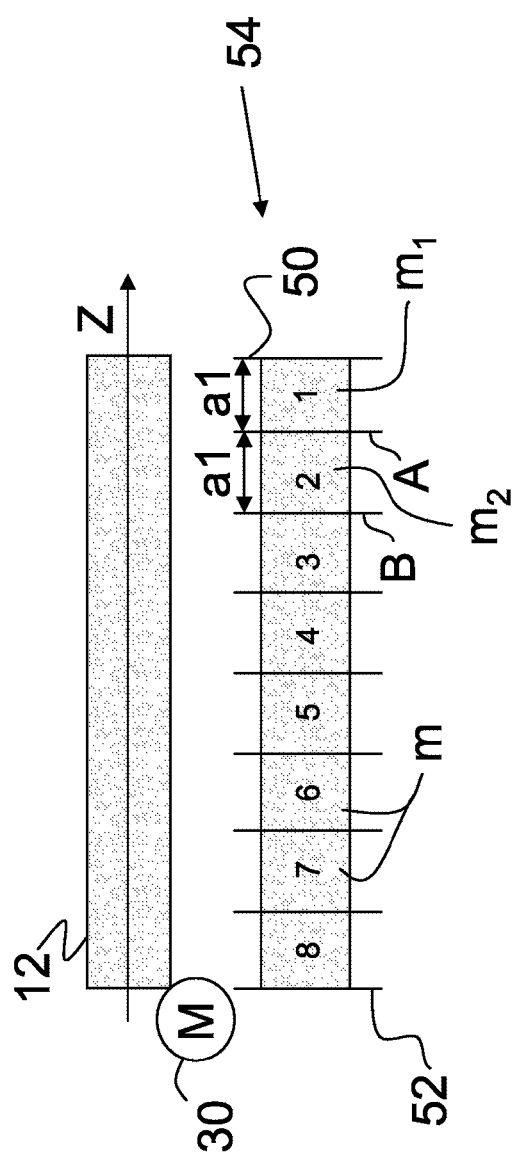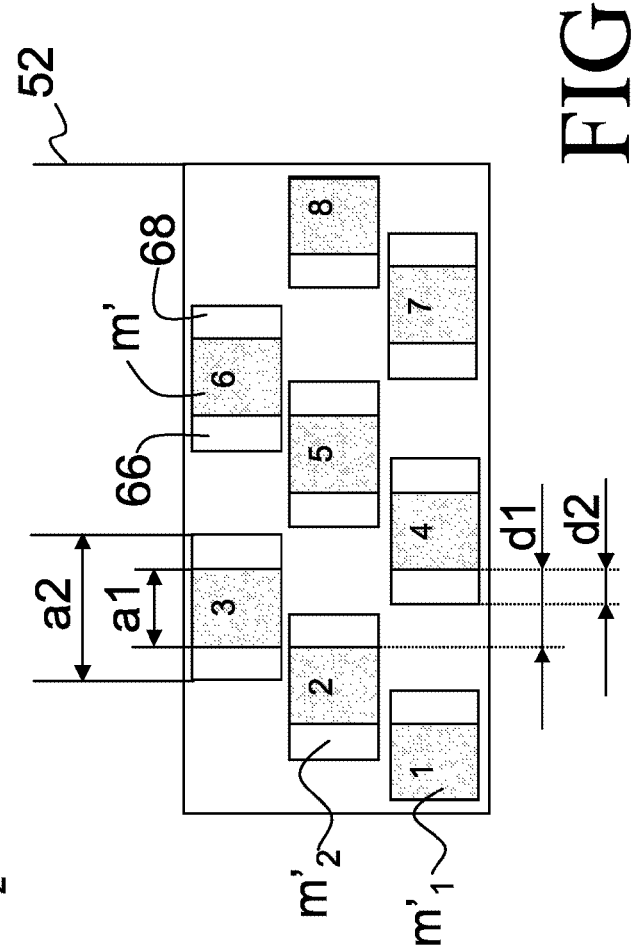

CONCURRENT RECONSTRUCTION USING MULTIPLE BED FRAMES OR CONTINUOUS BED MOTION

The present invention relates to the diagnostic imaging systems and methods. It finds particular application in conjunction with the Positron Emission Tomography (PET) scanners and will be described with particular reference thereto. It will be appreciated that the invention is also applicable to SPECT and other radiological scanners and the like.

PET is a valuable patient imaging technique employing positron emitting compounds. PET provides specific metabolic information about tissues that conventional scanners such as CT and MRI can not provide. Typically, PET scanners include a substantially circular bore that is surrounded by an array of detectors which detect coincidence events. Prior to the scan, the patient is injected with a positron emitting radioisotope which is taken up by cells. When a positron emits from a radioisotope, it combines with an electron to produce an annihilation reaction, in which the pair's mass is converted into energy. The energy is dispersed in the form of two 511 kev gamma rays or photons, traveling in 180 degrees opposite directions. When two detectors "see" 511 kev photons from the annihilation event concurrently or within nanoseconds of each other, the detectors register a coincidence along the line between the detector points—a line of response (LOR). The PET system draws lines of responses between each detection pair, registering coincidence events during the scan. When the scan is completed, areas with more intersecting lines indicate more concentrated areas of radioactivity. The system uses this information to reconstruct a three dimensional image of radioisotope distribution in the body.

In the PET whole body acquisition mode, the patient bed usually moves in a step-and-shoot fashion, i.e., after the data is acquired at one fixed bed position, the bed is moved to a new position to acquire the next data set. Such data acquisition is commonly called multiple bed frames. Typically, adjacent bed frames overlap one another to compensate for the decreased efficiency towards the axial edge of the detector. The data is saved as a 4D sinogram for each fixed bed frame. A 2D or 3D image reconstruction is performed for each bed frame separately. The reconstructed image frames are combined afterwards to form the whole body reconstruction. However, such reconstruction technique lacks data from other frames to enhance the reconstruction process which results in poor statistics at the edges of the frames. One solution is to combine all the data frames together at once, form a long axial length 4D sinogram, and reconstruct the whole body at once to improve the quality of the image.

This technique has certain drawbacks. First, a 3D iterative reconstruction algorithm needs to allocate memory for the 3D reconstructed object and 4D acquisition data. Combining all the data frames and reconstructing the whole body at once increases the computer memory requirement, and thus may slow down the reconstruction speed. Second, concurrent reconstruction (i.e., reconstructing while acquiring the data) is typically preferred in practice as it increases the patient throughput and/or minimizes the time to view the image after the data acquisition is completed. However, concurrent reconstruction and treating the whole body as one reconstruction object are not feasible for 3D iterative reconstruction algorithm, as all data frames are not available before the completion of the acquisition.

The present invention provides a new and improved imaging apparatus and method which overcomes the above-referenced problems and others.

In accordance with one aspect of the present invention, an imaging system is disclosed. An acquired sinogram of projection data of an entire object is loaded into a data memory. An object reconstruction means reconstructs an image representation of the entire object. A means extracts sinogram subsets of a prespecified axial length from the data memory one at a time. A sinogram subset reconstruction means sequentially reconstructs sinogram subsets one at a time into successive regions of a common entire object image.

In accordance with another aspect of the present invention, an imaging method is disclosed. A sinogram of projection data of an entire object is acquired. Sinogram subsets of a prespecified axial length are extracted from a data memory one at a time. Sinogram subsets are sequentially reconstructed one at a time into successive regions of a common entire object image.

One advantage of the present invention resides in reducing the statistics noise by reconstructing whole body scan as one object.

Another advantage resides in reducing the memory required for reconstruction of the whole body.

Another advantage resides in concurrent reconstruction while acquiring the data.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 3:
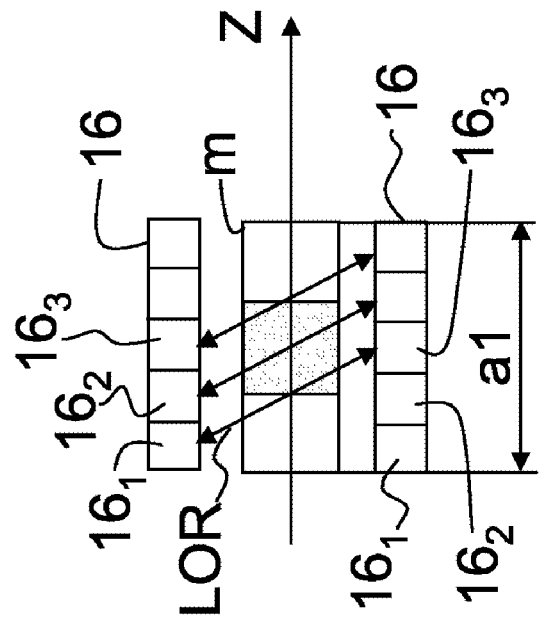
Figure 2:
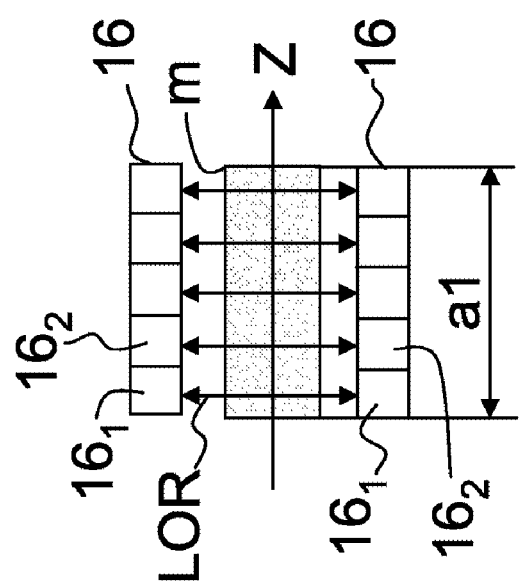
Figure 4:
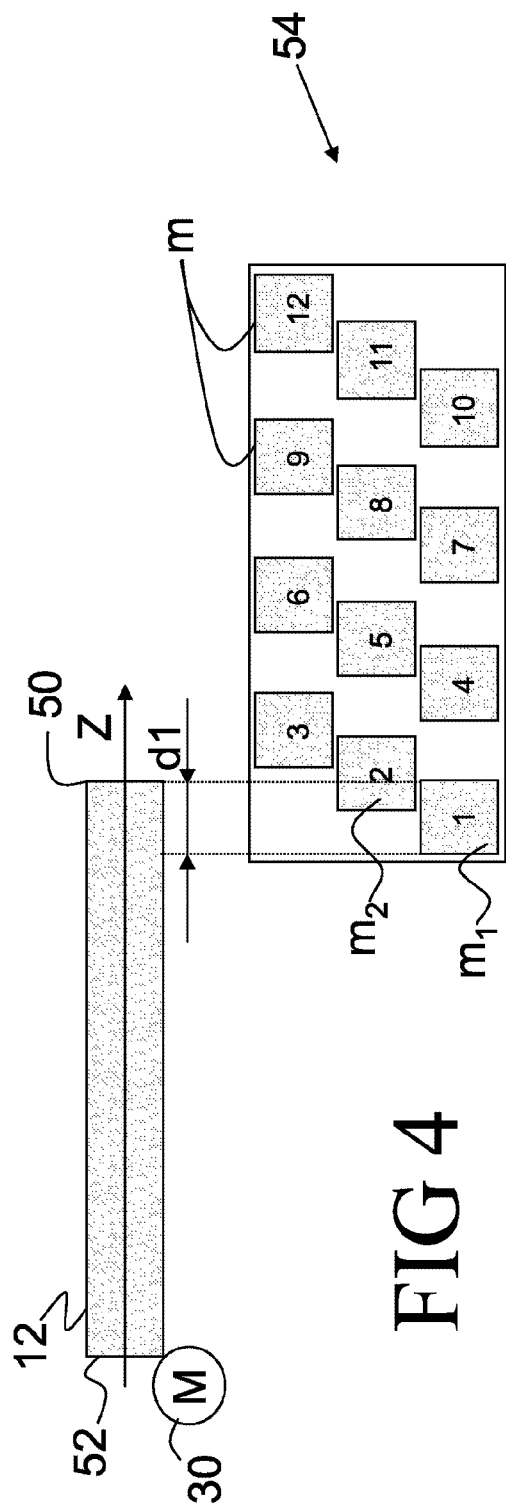
Figure 5:
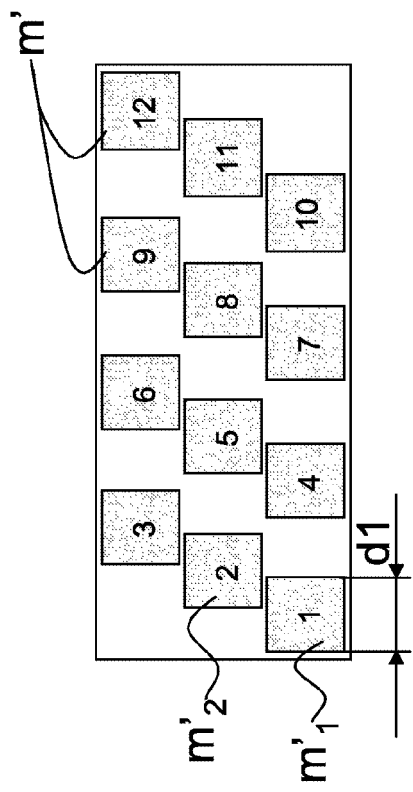
Figure 9:
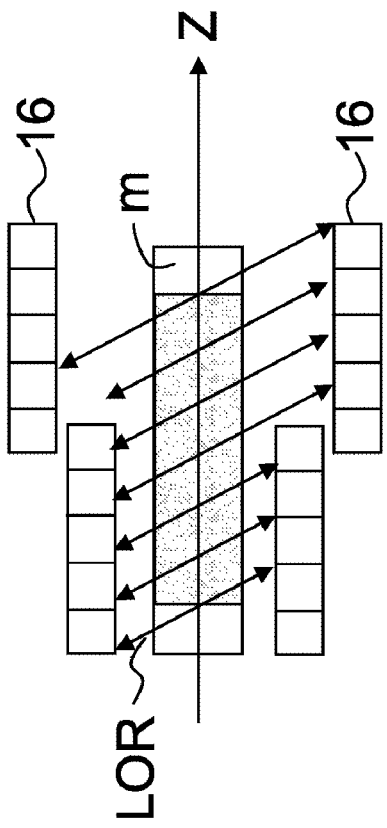
Figure 8:
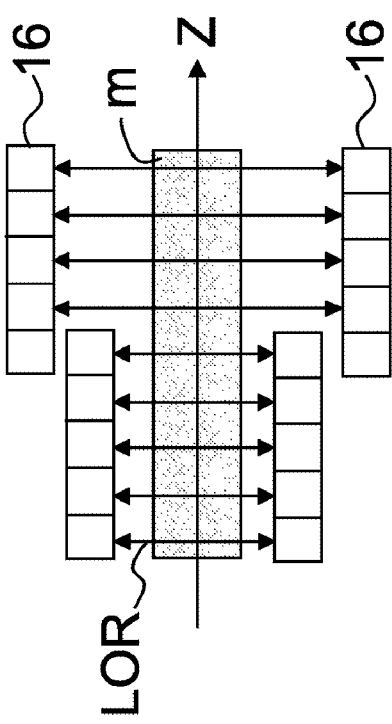
Figure 13:
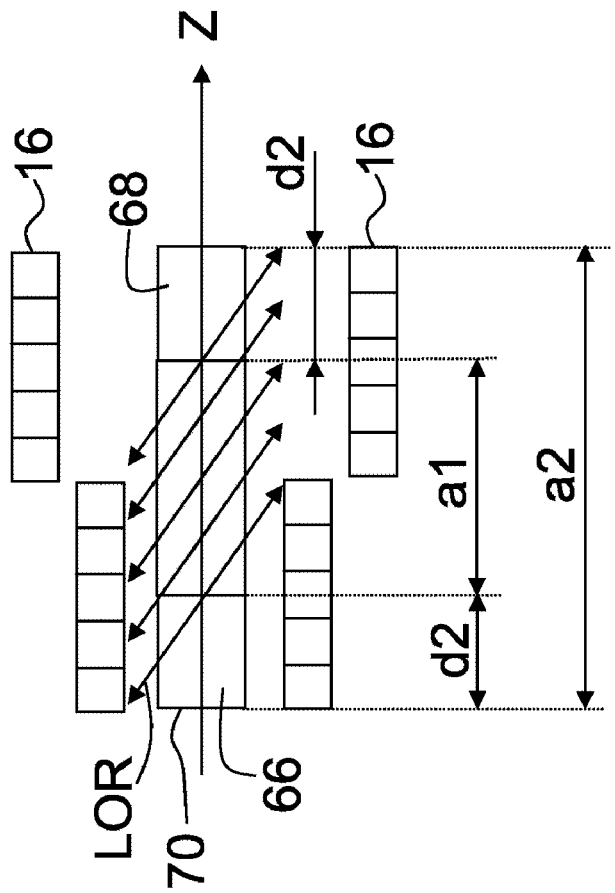
Figure 12:
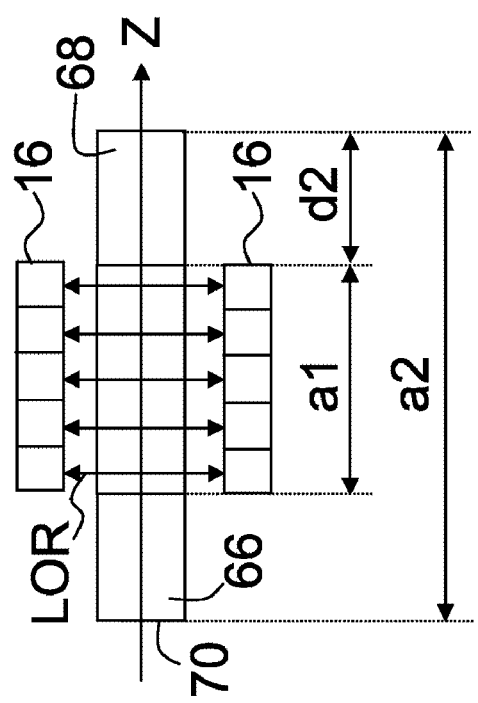
Figure 14:
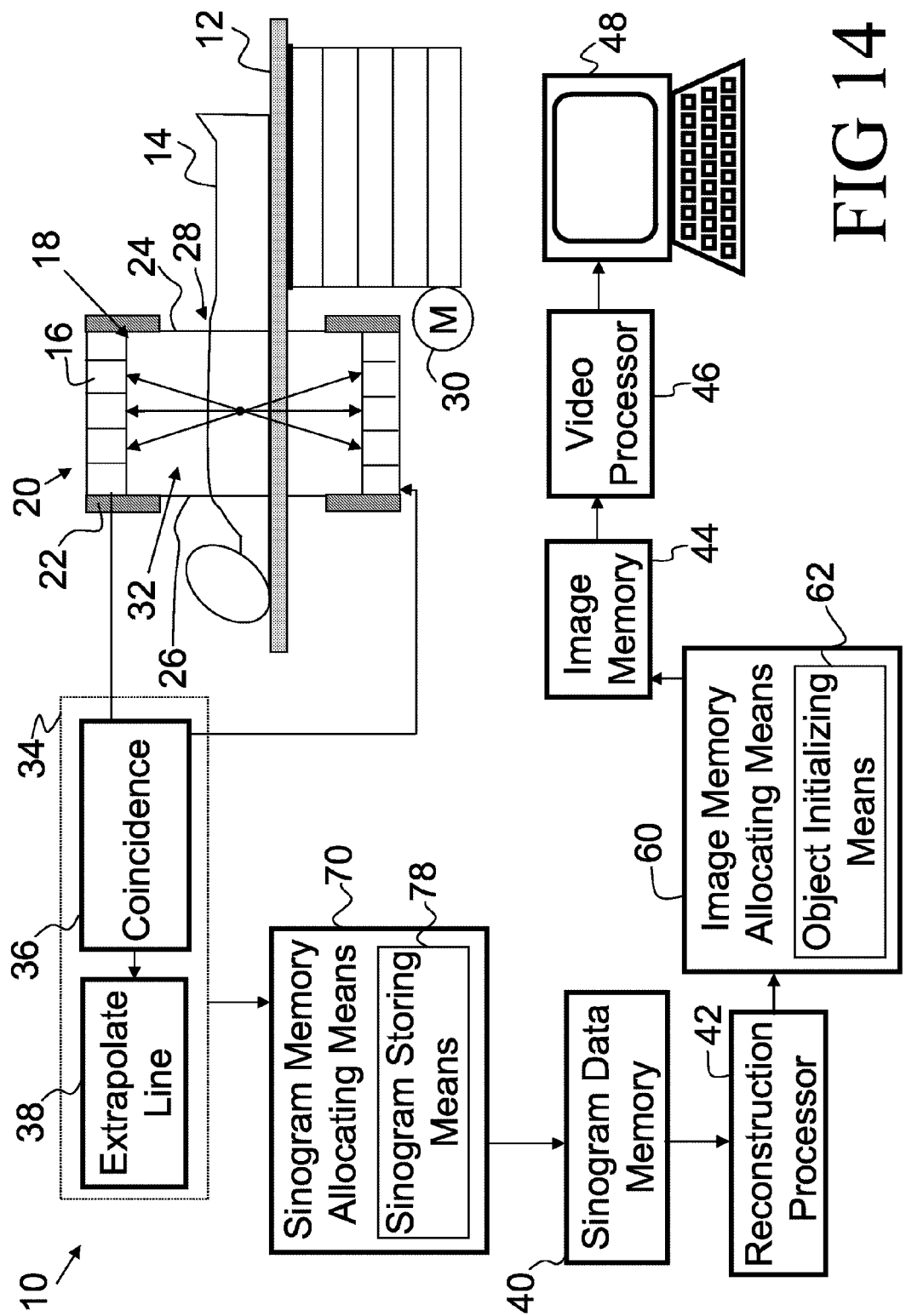
Figure 15:
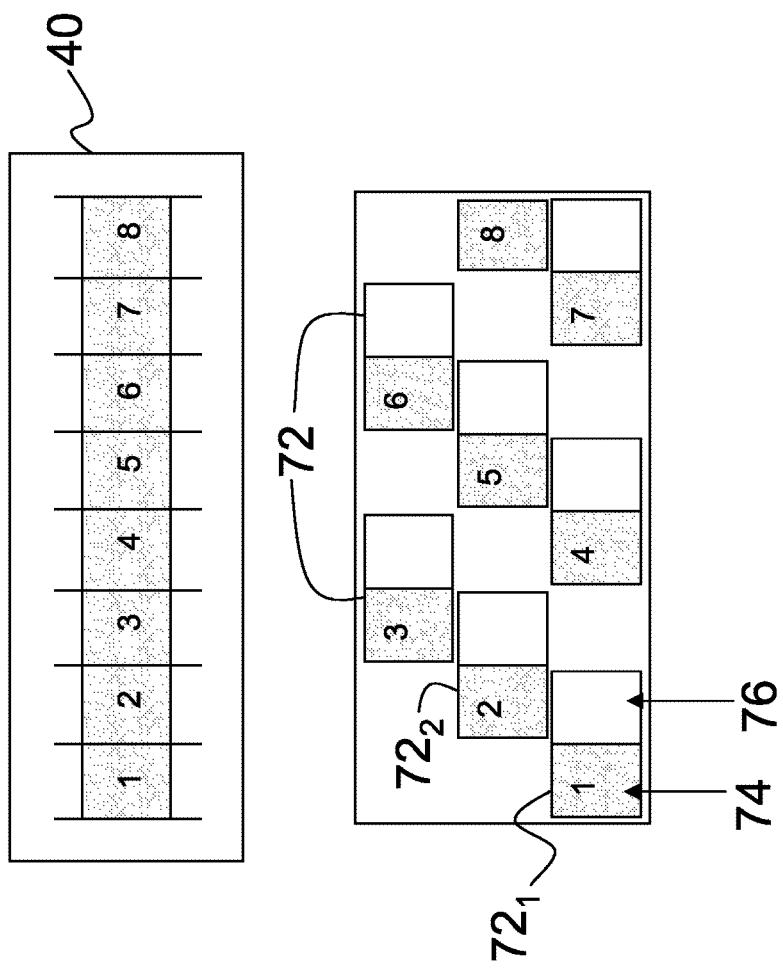

FIG. 1 is a diagrammatic illustration of an imaging system;

FIG. 2 diagrammatically illustrates zero tilt LOR;

FIG. 3 diagrammatically illustrates non-zero tilt LOR;

FIG. 4 diagrammatically illustrates sinogram subsets acquisition in a stop and shoot mode;

FIG. 5 diagrammatically illustrates reconstructed axial regions for each subset of FIG. 4;

FIG. 6 diagrammatically illustrates overlapping sinogram subsets acquisition in a continuous subject support motion mode;

FIG. 7 diagrammatically illustrates reconstructed axial regions for each subset of FIG. 6;

FIG. 8 diagrammatically illustrates zero tilt LOR for a continuous subject support motion mode of FIG. 6;

FIG. 9 diagrammatically illustrates non-zero tilt LOR for a continuous subject support motion mode of FIG. 6;

FIG. 10 diagrammatically illustrates non-overlapping sinogram subsets acquisition in a continuous motion;

FIG. 11 diagrammatically illustrates reconstructed axial regions for each subset of FIG. 10;

FIG. 12 diagrammatically illustrates zero tilt LOR for a continuous subject support motion mode of FIG. 10;

FIG. 13 diagrammatically illustrates non-zero tilt LOR for a continuous subject support motion mode of FIG. 10;

FIG. 14 is a diagrammatic illustration of a detailed portion of an imaging system; and FIG. 15 diagrammatically illustrates an acquisition scheme for a continuous subject support motion mode with equal axial acquisition regions.

With reference to FIG. 1, an imaging system 10 includes a subject support means 12, such as a table or couch, which supports a subject 14 being imaged. The subject 14 is injected with one or more radioisotopes to induce positron emission. A circularly cylindrical, annular array of detectors 16 is arranged around a bore 18 of a PET scanner 20 that defines an axial field-of-view. When the detectors have planar faces, the detector array 16 may be an octagon or other regular polygon that approximates a circle. The detector elements are preferably mounted in planar sub-arrays that are mounted end-to-end to define the detector array 16. Radiation end shields 22 are mounted at an entrance 24 and an exit 26 of the circular bore 18 to define a receiving area or entrance aperture 28 of the PET scanner 20.

A motor means 30, such as a motor and a drive, advances and/or retracts the subject support 12 to achieve the desired positioning of the subject 14 within an examination region 32 defined by the bore 18, e.g. with the region of interest centered in the field of view (FOV) of the detector array. Radiation events detected by detectors 16 are collected by a line of response (LOR) calculating circuit 34. The LOR calculator 34 includes a coincidence detector 36 that determines when two events are within a preselected temporal window of being simultaneous. From the position of the detectors 16 and the position within each detector, at which the coincident radiation was received, a ray between the radiation detection points is calculated by a line extrapolator 38.

With reference to FIG. 2, in an axial direction Z, the detector elements form rings $16_1, 16_2, \ldots, 16_n$. When the LOR rays have a zero tilt and extend between same ring of the detector, e.g. the ring $16_1$, the acquired data generates a direct sinogram. Such direct sinogram covers the data being acquired over the entire axial subset regional.

With reference to FIG. 3, LOR rays have a non-zero tilt and extend between different rings of the detector 16, e.g. between the ring $16_1$ and the ring $16_3$, resulting in an oblique or tilted sinogram. The oblique sinogram results in the data being acquired only over a part of the axial subset regional.

With continuing reference to FIG. 1, the data are saved in a sinogram format in a sinogram data memory or buffer 40. As will be discussed in a greater detail below, a data reconstruction processor or process 42 reconstructs an electronic image representation of a whole body of the subject 14 from subsets of the sinogram data stored in the data memory 40. The resultant image representation is stored in an image memory 44. Portions of the stored image representation are retrieved by a video processor 46 and converted to an appropriate format for display on a monitor 48, such as a video, CCD, active matrix, plasma, or other monitor. Of course, a color printer or other output device may also be used to present the data in a convenient format.

With continuing reference to FIG. 1 and further reference to FIG. 4, the scanner 20 performs the whole body scan and acquires fixed multiple overlapping data frames or sinogram subsets $m_1, m_2, \ldots, m_n$ in a stop and shoot mode. More specifically, the motor means 30 advances and hauls the subject support 12 in a repeated pattern in the axial direction Z from an initial position 50 to a final position 52. Each movement period, the motor means 30 moves the subject support a prespecified distance. During the idle periods of the motor means 30, the scanner 20 acquires a set 54 of the sinogram subsets $m_1, m_2, \ldots, m_n$ which set 54 represents the sinogram of the whole body of the subject 16. The axial length a1 of each sinogram subset $m_1, m_2, \ldots, m_n$ is preferably equal to the detector's 16 axial field of view d1. The movement distance is chosen to overlap each two adjacent sinogram subsets. The subsets $m_1, m_2, \ldots, m_n$ are stored in the sinogram data memory 40.

As the scanner 20 acquires the data set 54, the reconstruction processor 42 starts reconstructing the image using an iterative reconstruction technique, such as the ML-EM reconstruction. More specifically, a sinogram subset extracting means 58 loads the sinogram of the first subset $m_1$. An image memory allocating means 60 allocates an image space for each sinogram subset one at a time while the sinogram data is being loaded. An object initializing means 62 initializes the image memory 44. A sinogram subset reconstruction means 64 reconstructs the first subset $m_1$ using sinogram $\phi$ angle and/or tilt angle as a subset with one or few iterations. The reconstructed first subset $m'_1$ is stored in the image memory 44. In an iterative reconstruction, newly acquired data is used to "correct" the previously reconstructed image. For example, the previously reconstructed data is forward projected and compared with the newly acquired data. If the reconstructed image was perfect, the two would match. When the two do not match, the difference or error is determined and back projected to "correct" the reconstructed image. In this manner, the reconstructed image converges on a final image becoming more precise with each iteration.

Next, the sinogram subset extracting means 58 loads the sinogram corresponding to the second subset $m_2$. The object initializing means 62 initializes a part of the image memory 44 which corresponds to the non-overlapping portion of the second subset $m_2$. A portion of the second subset image $m_2$ that overlaps the first subset $m_1$ has been already reconstructed during the reconstruction of the first subset $m_1$. The sinogram subset reconstruction means 64 reconstructs the second subset $m_2$ using the corresponding reconstructed portion of the first subset $m_1$ as a first approximation of the final image while generating a first approximation image in the portion of the non-overlapping portion of the image memory corresponding to the second subset $m_2$. In this manner, with a 50% overlap, the first half of the image memory corresponding to the second subset $m_2$ (which half also corresponds to the first subset $m_1$) converges on the final image as an estimate of the image which is formed in the second half of the memory which corresponds to the second subset $m_2$. As seen in FIG. 5, each reconstructed axial region m' of each sinogram subset $m_1, m_2, \ldots, m_n$ corresponds the detector's 16 axial field of view d1.

The reconstructed partial image is stored in the image memory 44. The reconstruction process 42 is repeated for the subsets being acquired by the scanner 20 to obtain the image representation of the entire subject. Each data set is used to converge the estimated image portion from the previous data set while generating an estimated image portion for the next data set to converge. In this manner, only a portion of the whole body image memory corresponding to the size of the detector head is actively reconstructed at any given time.

With continuing reference to FIG. 1 and further reference to FIG. 6, the scanner 20 performs the whole body scan and acquires the overlapping sinogram subsets $m_1, m_2, \ldots, m_n$ while the motor means 30 continuously advances the subject support 12 in the axial direction Z from the initial position 50 to the final position 52. While the motor means 30 continuously moves the subject support 12, the data is binned into sinogram subsets $m_1, m_2, \ldots, m_n$, each of the axial length a1. The subsets $m_1, m_2, \ldots, m_n$ are stored in the sinogram image memory 40.

With continuing reference to FIG. 6 and further reference to FIG. 7, each two adjacent sinogram subsets in the sinogram subsets 54 as well as each two adjacent reconstruction regions m' overlap. The amount of axial overlap is preferably equal to the detector's axial FOV d1. The length a1 corresponding to each set is preferably longer than the FOV d1.

With reference again to FIG. 1 and continuing reference to FIG. 6, as the scanner 20 acquires the data set 54, the reconstruction processor 42 starts reconstructing the image. The sinogram subset extracting means 58 loads the sinogram for the first subset $m_1$ which corresponds to the continuous subject support movement from the initial position 50 to a position A. The object initializing means 62 initializes the image memory 44. The sinogram subset reconstruction means 64 reconstructs the first subset $m_1$ using sinogram $\phi$ angle and/or tilt angle as a subset with one or few iterations. The reconstructed first subset $m'_1$ is stored in the image memory 44.

Next, the sinogram subset extracting means 58 loads the sinogram corresponding to the second subset $m_2$ which corresponds to the data acquired during continuous subject support movement from the position A to a position B. The object initializing means 62 initializes a part of the image memory 44 which corresponds to the non-overlapping portion of the second subset $m_2$. The portion of the second subset $m_2$ that was already reconstructed during the reconstruction of the first subset $m_1$ is not initialized. The sinogram subset reconstruction means 64 reconstructs the second subset $m_2$ into the whole body image memory converging the portion that was estimated by the first subset $m'_1$ into a final image portion and estimates the other portion. The reconstructed partial image representation is stored in the image memory 44. The reconstruction process 42 steps the reconstruction window along the image memory for the remaining subsets. The window of the image memory into which data is reconstructed moves continuously in synchronization with the patient couch 12.

With reference to FIGS. 2 and 3, a direct sinogram results in a greater coverage of the subject 14, while an oblique sinogram results in a smaller coverage of the patient 14. With reference to FIGS. 8 and 9, even with the continuous motion, the subsets lack oblique data near the axial edges. Each tilted or oblique sinogram is sparse and requires more memory storage by adding all sinogram frames. The oblique sinograms preferably are reconstructed over smaller windows, e.g. windows that span the fully sampled region.

With reference again to FIG. 1 and further reference to FIGS. 10-13, the scanner 20 performs the whole body scan and acquires multiple fixed data frames or sinogram subsets $m_1, m_2, \ldots, m_n$ while the motor means 30 continuously advances the subject support 12 in the axial direction Z from the initial position 50 to the final position 52. Each zero-tilt sinogram subset $m_1, m_2, \ldots, m_n$, as shown in FIG. 12, is selected to be a fixed axial length a1 with no overlaps. In one embodiment, the length a1 of each zero-tilt sinogram subset is selected to be equal to the detector's axial FOV d1. Of course, it is also contemplated that the selected axial length a1 can be greater or smaller than the detector's axial FOV d1. Each maximum tilt sinogram subset $m_1, m_2, \ldots, m_n$ of the set 54 is continuously acquired as a motor means 30 continuously moves the subject support 12 over a distance a2 which is the distance needed to fully sample regional at the maximum tilt. In leading and trailing regions 66, 68 where d2=(a2−a1)/2, the data at intermediate tilts is partially sampled. The distance d2 is preferably equal to one half of the detector axial FOV d1.

The reconstructed window of the whole body image memory covers the region a2 with the regions a1 of successive scans abutting but not overlapping or spaced. The leading region 66 of the data set makes an initial estimate of the image in that region. Because the undersampling is greatest toward a leading edge 70 and least toward the axial regional, the quality of the estimate image varies accordingly.

When the second region $m'_2$ is reconstructed, the regional of the second set $m_2$ builds on the available estimated image from the preceding region $m'_1$. The leading region 66 of the second set $m_2$ makes further refinements to the overlapping trailing portion 68 of the axial regional of the preceding set $m'_1$. Again, the refinements are strongest where the data is the least undersampled. In this manner, the undersampled data in the regions 66, 68 are used to smooth the interfaces between adjoining fully sampled regions a1. Therefore, each two consecutive reconstruction axial subset regions $m'_1, m'_2$ overlap with each other by the detector's axial FOV d1. In this embodiment, the total storage of the sinogram is kept to a minimum.

With reference again to FIGS. 10 and 11, and further reference to FIGS. 14 and 15, a sinogram subset memory allocating means or process 70 allocates memory space sections 72 one at a time while the scanner 20 acquires the data set 54. Each memory space section 72 is initially allocated to be equal to a2, e.g. the sinogram axial subset length a1 plus the detector's axial FOV d1, and includes first and second portions 74, 76. As the motor means 30 moves the subject support 12 from the initial position 50 to the position A the selected axial distance a1, the first subset $m_1$ of the length a1 along with an additional length d1 are acquired by the scanner 20. A storing means 78 saves the first axial sinogram set $m_1$ of the length a2 into the first and second portions 74, 76 of a first section $72_1$. At this point, the first portion of the first set $m_1$ saved into the first portion 74 is complete. The data from the first portion 74 are stored in the sinogram data memory 40, while the second portion 76 of the first section $72_1$, which holds incomplete data of the first set $m_1$, is moved to the first portion 74 of a second section $72_2$. The storing means 78 initializes to zero the second portion 76 of the first memory section $72_1$ that is not filled anymore with the first sinogram subset $m_1$. The second memory section $72_2$ is allocated such that it includes the first portion 74 previously filled with the incomplete of the first subset $m_1$ and the initialized second portion 76. Meanwhile, the motor means 30 moves the subject support 12 from the position A to the position B the selected axial distance a1 to acquire the second subset $m_2$ and the additional length d1 by the scanner 20. The storing means 78 saves the second axial sinogram set $m_2$ into the allocated (as described above) second memory section $72_2$. The sinogram subset memory allocating process 70 is repeated in the described fashion to allocate the memory space sections 72 for the rest of the sinogram subsets.

When only the last sinogram subset remains to be stored, the subset memory allocating means 70 allocates the memory space section $72_n$ equal to the axial length a1.

Of course, it is also contemplated that the memory allocating process 70 is utilized appropriately with other modes of data acquisition as discussed above, e.g. the stop and shoot mode of FIGS. 4 and 5 and/or the continuous overlapping mode of FIGS. 6 and 7.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An imaging system comprising:
    a data memory into which an acquired sinogram of projection data of an entire object is loaded; and
    an object reconstruction processor which reconstructs a volumetric image representation of the entire object in successive volumetric image portions, which reconstruction processor is programmed to:
    extract sinogram subsets each corresponding to a prespecified axial length from the data memory one at a time, the prespecified axial lengths partially overlapping,
    sequentially reconstruct sinogram subsets into the successive volume image portions with an iterative reconstruction algorithm using a trailing portion of a preceding image portion as an initial estimate for a leading edge portion of a currently reconstructed image portion of the image and reconstructs the trailing edge portion of the currently reconstructed image portion to be used as an initial estimate for a leading edge portion of a next subsequent image portion.

2. The system as set forth in claim 1, wherein the reconstruction processor is programmed to iteratively correct the initial estimates of image portion with the sinogram subsets.

3. The system as set forth in claim 1, wherein each image portion is a volume image portion including a plurality of slices.

4. The system as set forth in claim 1, further including:
a motor which repeatedly advances a subject support, which carries the object, a prespecified axial distance; and
a scanner which acquires sinogram data during idle periods between advances to generate a set of the sinogram subsets each subset corresponding to the prespecified axial length.

5. The system as set forth in claim 4, wherein the motor advances the subject support such that adjacent sinogram subsets overlap each other to account for a non-zero tilt sinogram.

6. The system as set forth in claim 4, wherein the sinogram subset axial length is equal to a field of view of the scanner.

7. The system as set forth in claim 1, further including:
a motor which continuously advances a subject support, which carries the object, from an initial position to a final position; and
a scanner which acquires sinogram data during the continuous motion of the subject support and generates a set of the sinogram subsets each subset corresponding to the prespecified axial length.

8. The system as set forth in claim 7, wherein adjacent sinogram subsets overlap each other by an overlap which accounts for non-zero tilt sinograms.

9. The system as set forth in claim 7, wherein the adjacent sinogram subsets overlap a distance which is equal to a field of view of the scanner.

10. The system as set forth in claim 1, further including:
a motor which advances a subject support, which carries the object, from an initial position to a final position; and
a scanner which acquires sinogram data from the subject to generate a set of the sinogram subsets which each has a selected fixed axial length equal to at least a third of a field of view of the scanner.

11. The system as set forth in claim 10, wherein the trailing portion and the leading edge portion each has an axial length equal to one half a field of view of the scanner.

12. The system as set forth in claim 10, wherein the scanner is a PET scanner.

13. An imaging method comprising:
extracting sinogram subsets corresponding to a prespecified axial length from a data memory one at a time which data memory holds sinogram data acquired over a region of an object;
applying an iterative reconstruction algorithm to each of the sinogram subsets in which an estimated image is iteratively improved to converge on a final image, including: applying an iterative algorithm to each of the sinogram subsets in which an estimated image is iteratively improved to converge on a final image of the region of the object, including:
(a) applying the iterative reconstruction algorithm to a given one of the sinogram subsets to estimate a portion of a current image section using a portion of a preceding image section, and finishing the portion of the preceding image section; and
(b) repeating step (a) to apply the iterative reconstruction algorithm to the plurality of sinogram subsets to reconstruct the final image of the region of the object.

14. The method as set forth in claim 13, wherein the step of applying the iterative reconstruction algorithm further includes:
estimating a first image portion of an $n^{th}$ image section and finalizing a second image portion of a an $(n-1)^{th}$ image section by applying the iterative reconstruction algorithm to an $n^{th}$ of the sinogram subsets;
estimating the first image portion of an $(n+1)^{th}$ image section and finalizing the second image portion of the $n^{th}$ image section by applying the iterative reconstruction algorithm to an $(n+1)^{th}$ of the sinogram subsets.

15. The method as set forth in claim 14, wherein the step of applying the iterative reconstruction algorithm further includes:
estimating the first image portion of an $(n+2)^{th}$ image section and finalizing the second portion of the $(n+1)^{th}$ image section by applying the iterative reconstruction algorithm to an $(n+2)^{th}$ of the sinogram subsets.

16. The method as set forth in claim 13, further including:
continuously advancing a subject support, which carries the object, from an initial position to a final position;
with a scanner, acquiring the sinogram data during the continuous motion of the subject support; and
storing the sinogram data in the data memory.

17. The method as set forth in claim 16, wherein each image section corresponds to a length of a field of view of the scanner.

18. The method as set forth in claim 16, wherein the adjacent image sections overlap by 50%.

19. The method as set forth in claim 16, further including:
allocating memory space sections to each sinogram subset being acquired by the scanner including:
storing a first acquired sinogram subset into the data memory,
compressing the first acquired subset into a first section portion to release a second section portion, and
allocating the released second section portion for a storage of subsequently acquired second sinogram subset.

20. A diagnostic imaging system comprising:
a scanner which acquires the sinogram data; and
one or more processors programmed to perform the method of claim 13.

21. The method as set forth in claim 13, wherein each portion is a multi-slice volume.

22. An imaging method comprising:
continuously advancing a subject support;
with a scanner, acquiring sinogram data of an object during the continuous motion of the subject support;
storing the sinogram data in a data memory;
extracting sinogram subsets corresponding to a prespecified axial length from the data memory one at a time;
sequentially reconstructing each of the sinogram subsets one at a time into successive volume image sections corresponding to successive regions of the object, each region of the object having an axial length equal to at least a half of a field of view of the scanner;
wherein the step of reconstructing further includes: initially estimating an image portion adjacent a leading edge one image section and finalizing an image portion adjacent a trailing edge of a preceding image section.

23. The method as set forth in claim 22, wherein the step of reconstructing includes:
applying an iterative reconstruction in which estimated volume image sections are iteratively improved to converge on a final image.

* * * * *